United States Patent
Cantu et al.

[11] Patent Number: 5,635,728
[45] Date of Patent: Jun. 3, 1997

[54] ROTATING SCANNER SYSTEM FOR READING MULTIPLE STORAGE LAYER RADIATION SCREENS

[75] Inventors: Gary R. Cantu, San Jose; Joseph R. Rimsa, Milpitas; Ezra Van Gelder, Palo Alto; Daniel B. Steinberg, Campbell, all of Calif.; Iain H. Hueton, Ogden, Utah

[73] Assignee: Denoptix, Inc., Sunnyvale, Calif.

[21] Appl. No.: 493,109

[22] Filed: Jun. 19, 1995

[51] Int. Cl.$^6$ .................................................. G01N 23/04
[52] U.S. Cl. .......................... 250/584; 250/585; 250/590
[58] Field of Search ...................................... 250/584, 585, 250/586, 590, 583, 589

[56] References Cited

U.S. PATENT DOCUMENTS

| | | | |
|---|---|---|---|
| 4,302,671 | 11/1981 | Kato et al. | 250/585 |
| 4,543,479 | 9/1985 | Kato | 250/590 |
| 4,582,989 | 4/1986 | Agano | 250/347 |
| 4,692,813 | 9/1987 | Conrad et al. | |
| 4,816,923 | 3/1989 | Saotome | |
| 4,882,488 | 11/1989 | Hashiue | |
| 4,973,134 | 11/1990 | Finkenzeller et al. | 250/584 |
| 4,992,102 | 2/1991 | Katayama | |
| 5,003,570 | 3/1991 | Whiting | 250/583 |

FOREIGN PATENT DOCUMENTS

WO94/27167  11/1994  WIPO .

*Primary Examiner*—Carolyn E. Fields
*Attorney, Agent, or Firm*—Wilson Sonsini Goodrich & Rosati

[57] ABSTRACT

A system is provided for reading an image stored on a storage layer radiation screen. The system includes a carousel for holding a storage layer radiation screen and a screen scanning system. The screen scanning system includes a carousel mount on which the carousel may be mounted and a rotation mechanism for rotating the carousel mount, rotation of the carousel mount serving to rotate the carousel about a rotational axis which, in turn, causes the screens held on the carousel to move in a circular path about the rotational axis. The carousel is preferably removable from the carousel mount. The screen scanning system also includes an image acquisition optical system positioned adjacent the circular path of the screen, the image acquisition optical system including an excitation system for focusing an excitation beam on a portion of the screen to cause a light emission, and an emission collecting system for collecting the light emitted from the screen. The screen scanning system may further include an optics driver for moving the image acquisition optical system in a direction parallel to the rotational axis of the carousel. A method is provided for reading images stored on multiple storage layer radiation screens. The method includes attaching multiple storage layer radiation screens to a carousel, rotating the carousel about a rotational axis such that the screens move in a circular path about the rotational axis, focusing an excitation beam at a point on the circular path such that the portions of the screens passing the point on the circular path emit light, collecting the light emitted, and moving the point on the circular path on which the excitation beam is focused in a direction parallel to the rotational axis.

35 Claims, 9 Drawing Sheets

ROTATING SCANNER SYSTEM FOR READING MULTIPLE STORAGE LAYER RADIATION SCREENS

BACKGROUND OF THE INVENTION

1. Field of the Invention

The present invention relates to a system and method for reading radiation images stored on storage layer radiation screens. More specifically, the present invention relates to a system and method for reading multiple storage layer radiation screens positioned on a rotating carousel.

2. Description of Related Art

A variety of storage layer radiation screens have been developed for recording radiation images created by exposing the screen to a radiation source, such as x-rays, α-rays, β-rays, γ-rays, cathode rays and ultraviolet rays. When radiation is passed through an object onto the screen, the radiation forms a latent radiation image on the screen by stimulating the storage layer. This latent radiation image can then be road by scanning the screen using a suitable electromagnetic wave radiation, such as visible light or infrared rays (hereinafter referred to as "stimulating rays"), which releases the radiation energy stored in the storage layer as a light emission. The light emitted from the storage layer is then detected and converted into data corresponding to the image. Elimination of the image stored in the storage layer may be accomplished by exposing the storage layer for a period of time to a suitable electromagnetic wave radiation.

One type of storage layer radiation screen stores the radiation image in the form of an electrical charge distribution at a photo semiconductor layer. An example of this type of storage layer is described in *Journal of Applied Photographic Engineering* 4 178–182 (1978). Another type of storage layer radiation screen employs a luminophore, such as a phosphorescent material, which becomes excited when exposed to radiation. When the luminophore is exposed to stimulating rays, such as visible light, the luminophore releases energy in the form of light, Examples of this type of storage layer are described in U.S. Pat. Nos. 3,859,527 and 4,346,295 which are incorporated herein by reference.

As described in U.S. Pat. Nos. 4,258,264, 4,276,473, 4,315,318 and 4,387,428, stimulable phosphors have been proposed for use as luminophores in radiation image recording and reproducing systems. According to these systems, a screen containing a layer of a stimulable phosphor is exposed to radiation which has passed through an object being imaged, such as a part of the human body. The screen is then scanned with stimulating rays, such as a laser beam, which causes the phosphors in the screen to emit light in proportion to the amount of radiation absorbed by the portion of the screen being scanned. The light emitted by the screen is then detected and converted into an electrical signal. The electrical signal is then used to reproduce the radiation image as a visible image.

Storage layer radiation screens, such as stimulable phosphor screens, generally include a layer of stimulable material dispersed in an appropriate binder material. When the storage layer is self-supporting, the storage layer may itself form the storage layer radiation screen. However, the storage layer radiation screen generally includes a layer of stimulable material which is placed on a suitable substrate. For example, stimulable phosphor screens generally include an adhesive layer for binding the phosphor layer to the substrate. Stimulable phosphor screens can also include a protective layer formed on the phosphor layer surface opposite the substrate for physically and chemically protecting the phosphor layer. Stimulable phosphor screens can also include a light-reflecting layer between the phosphor layer and the substrate to improve the sensitivity of the screen. Alternatively, stimulable phosphor screens can include a light-absorbing layer between the phosphor layer and the substrate to improve the sharpness of the image produced by the storage phosphor screen. Colored or white particles have also been included in the phosphor layer to improve the sharpness of the image obtained.

One particular application for radiation screens employing a storage layer, such as a stimulable phosphor, is in the area of dental radiography. Storage layer radiation screens have the significant advantage of requiring lower x-ray radiation levels to produce the radiation image. As a result, the amount of x-ray radiation that a patient is exposed to when a storage layer radiation screen is used is significantly reduced, thereby reducing the health risks associated with x-ray radiography. In addition, storage layer radiation screens can provide images with higher resolution than are provided by conventional dental x-ray films.

Storage layer radiation screens can be more expensive to produce than traditional dental radiation films and require a device to read the image stored on the screens. In order for storage layer radiation screens to replace traditional dental radiation screens, it is important that the storage layer radiation screens be reusable. It is also important that the screens be easy to use and read. Accordingly devices are needed which facilitate the rapid, user-friendly reading of radiation images stored on these screens.

Devices for reading storage layer radiation screens generally read only one screen at a time and are limited in the size of the screen that can be read. A need exists for a screen reading device which is capable of simultaneously reading multiple screens of the same or different sizes. A need also exists for a removable sample holder so screens can be loaded onto one or more sample holders while other screens are being read.

Devices for reading storage layer radiation screens are also generally designed to read the screen in a linear manner where a screen scanner is rastered back and forth across the screen in order to read the entire surface of the screen. Devices which read screens using a rastered scanning motion generally require a greater amount of time to read than traditional dental x-ray film which requires 300 seconds to process. A need therefore exists for a device which can read storage layer radiation screens at a rate comparable to the time required to read traditional dental x-ray film.

SUMMARY OF THE INVENTION

A system is provided for reading an image stored on a storage layer radiation screen. The system includes a carousel for holding a storage layer radiation screen and a screen scanning system. The screen scanning system includes a carousel mount on which the carousel may be mounted and a rotation mechanism for rotating the carousel mount, rotation of the carousel mount serving to rotate the carousel about a rotational axis which, in turn, causes the screens held on the carousel to move in a circular path about the rotational axis. The carousel is preferably removable from the carousel mount. The screen scanning system also includes an image acquisition optical system positioned adjacent the circular path of the screen, the image acquisition optical system including an excitation system for focusing an excitation beam on a portion of the screen to cause a light emission, and an emission collecting system for collecting the light emitted from the screen.

The screen scanning system may further include an optics driver for moving the image acquisition optical system in a direction parallel to the rotational axis of the carousel. The image acquisition optical system is preferably positioned within about 20 mm of the circular path of the screen, more preferably within about 10 mm of the circular path of the screen. The excitation system preferably focuses the excitation beam on a portion of the screen having a diameter between about 30 and 200 microns, more preferably between about 35 and 50 microns. The rotation mechanism preferably rotates the carousel at least about 60 revolutions per minute, more preferably at least about 300 revolutions per minute.

The carousel may hold multiple storage layer radiation screens having the same size or different sizes. The carousel may also include a screen holder for holding the storage layer radiation screen which is removable from carousel. The screen holder may hold multiple storage layer radiation screens having the same size or different sizes.

A method is also provided for simultaneously reading images stored on multiple storage layer radiation screens. The method includes attaching multiple storage layer radiation screens to a carousel, rotating the carousel about a rotational axis such that the screens move in a circular path about the rotational axis, focusing an excitation beam at a point on the circular path such that the portions of the screens passing the point on the circular path emit light, collecting the light emitted, and moving the point on the circular path on which the excitation beam is focused in a direction parallel to the rotational axis.

BRIEF DESCRIPTION OF THE DRAWINGS

FIG. 2A illustrates the screen holder and carousel as an unified body where the carousel is removable from the screen scanning system.

FIG. 2B illustrates the screen holder as a series of screen holding mechanisms which can be removably attached to the carrousel.

FIG. 3A illustrates the use of physically complementary anchoring elements incorporated onto the screen holder and the back of the screen such that the screen is held to the screen holder by the union of the complementary anchoring elements.

FIG. 3B illustrates the use of magnetically complementary anchoring elements incorporated onto the screen holder and the back of the screen such that the screen is held to the screen holder by the union of a magnet and a piece of ferromagnetic material.

FIG. 3C illustrates the screen holder as including guide rails between which the screen is positioned in order to mount the screen onto the screen holder.

DESCRIPTION OF THE PREFERRED EMBODIMENTS

Figure 1:
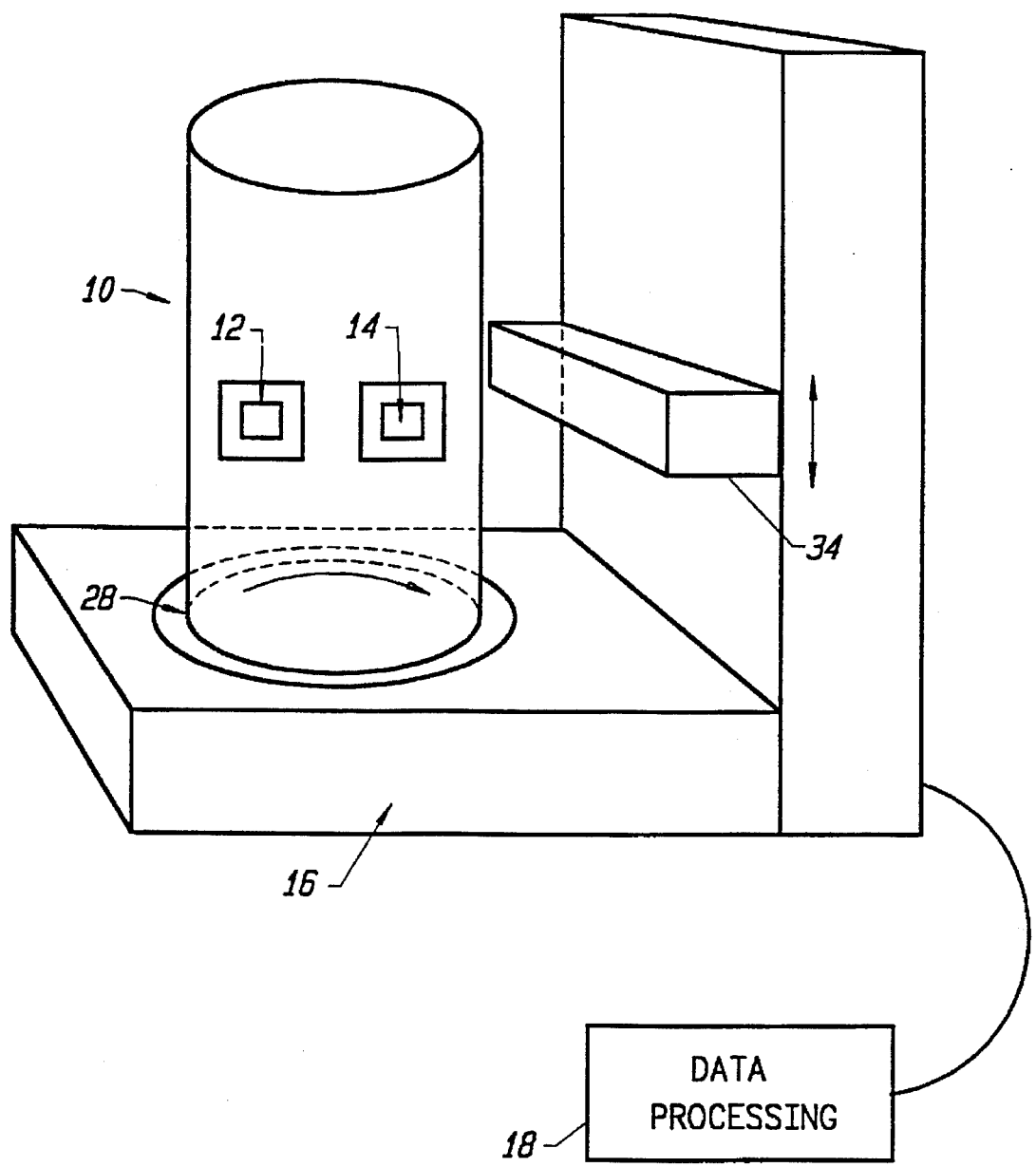
FIG. 1 illustrates a screen reading system according to the present invention.

The present invention relates to a system and method for simultaneously reading multiple storage layer radiation screens. The multiple screens can be the same size be of different sizes. The present invention also relates to a radiation screen reading system and method in which groups of screens can be loaded onto one or more screen holders which are removable from the screen reading system and can be manually or automatically introduced into the screen reading system for processing.

According to the system and method of the present invention, a screen holder is used which can hold one or more storage layer radiation screens. The screen holder is attached to a carousel which is rotated by the screen reading system about the carousel's rotational axis $\phi$, thereby causing the screen to be rotated about the carousel's rotational axis. The screen is preferably rotated about the carousel's rotational axis at a speed of at least 60 revolutions per minute, more preferably at least 300 revolutions per minute.

A screen scanning system is positioned outside the circle formed by the path of the screen as the carousel is rotated and is preferably positioned within about 20 mm of the circumference of the circle formed by the path of the screen, more preferably within about 10 mm of the circumference. Rotation of the carousel, and hence the one or more screens attached to the carousel, causes the screen scanning system to scan over a narrow line-shaped area of the screen perpendicular to the carousel's rotational axis. As the carousel is rotated, the screen scanner may also be moved by an optics driver in a direction parallel to the carousel's rotational axis. This enables the screen scanner to scan over different narrow line-shaped areas of the screen as the carousel is rotated, thereby enabling the entire surface area of the screen to be scanned.

Use of a rotating carousel provides an enhanced duty cycle for the screen reading system which, in turn, enhances the speed with which multiple screens can be processed. Accordingly, multiple screens can be scanned by the screen reading system at a speed comparable to traditional dental x-ray film readers.

By using a rotating carousel, one is also able to adjust the rotation rate of the carousel, the scan speed of the image acquisition optical system as well as the sampling size of the screen reading system while the screen reading system is in operation. This enables the screen reading system to be tuned and aligned in real time.

The screen holder may be designed to be removable from the radiation screen reading system by making the screen holder removable from the carousel. Alternatively, the carousel may be designed to be removable from the radiation screen reading system, removal of the carousel serving to also remove the screen holder. The removability of the screen holder or carousel from the screen reading system facilitates sample processing by the user.

The removability of the screen holder also enables multiple screen holders to be used with a single screen reading system. As a result, screens can be loaded into a screen holder as other screens are being scanned by the screen reading system. This increases the speed by which screens can be processed. In one embodiment, the screen reading system is adapted to automatically load a series of screen holders (or removable carrousels each including a screen holder) from a que into the screen reading system. This greatly increases the number of screens that can be loaded and read by the system at one time, thereby reducing the labor required for screen processing.

The removability of the screen holder also simplifies the screen handling process by the user. Each of the multiple screen holders can be designed to include an identification system, such as a bar code, which can be used to facilitate the identification of multiple screens.

The removability of the screen holder provides the further advantage that a variety of different screen types and sizes may be used with the device of the present invention. Accordingly, one is able to use different screen types and sizes for different applications. The capability of simultaneously scanning screens of different sizes is also provided by the system of the present invention.

The screen reading system includes a screen scanning system which reads the image stored on the screen. The screen scanning system includes an excitation system which provides an excitation beam to excite a portion of the storage layer of the screen and an emission collecting system which collects light emitted by the excited portion of the storage layer and converts the light collected into an electrical signal.

The electrical signal produced by the screen scanning system is communicated to a data processing system which assembles the data collected and provides the user with one or more outputs corresponding to the image stored on the screen. For example, the data processing system can be connected to a data storage device (floppy disc, hard drive, floptical), an image reproducing device (monitor, printer), as well as a variety of communication devices (modem, network). The data processing system also enables the data collected to be manipulated by the user.

An embodiment of the screen reading system and method of the present invention is discussed herein in greater detail.

FIG. 1 illustrates an embodiment of the screen reading system. As illustrated in FIG. 1, the screen reading system includes a carousel 10 having a screen holder 12 on which one or more screens 14 can be placed. The screen reading system also includes a screen scanning system 16 which includes a carousel mount for rotating the carousel, and an image acquisition optical system 34 for scanning the image stored on the screen 14. The image acquisition optical system 34 produces an electronic signal corresponding to the image stored on the screen 14. The screen reading system also includes a data processing system 18 for processing the electronic signal generated by the image acquisition optical system 34.

The screen holder 12 is preferably removable from the screen reading system 16 and is preferably capable of holding multiple screens. The screen holder 12 is also preferably capable of simultaneously holding one or more different sized screens. The screen holder 12 may be removably mounted on the carrousel 10. Alternative, the screen holder 12 may be fixed to the rotating carrousel 12 which is itself removable from the screen scanning system 16.

Figure 2B:
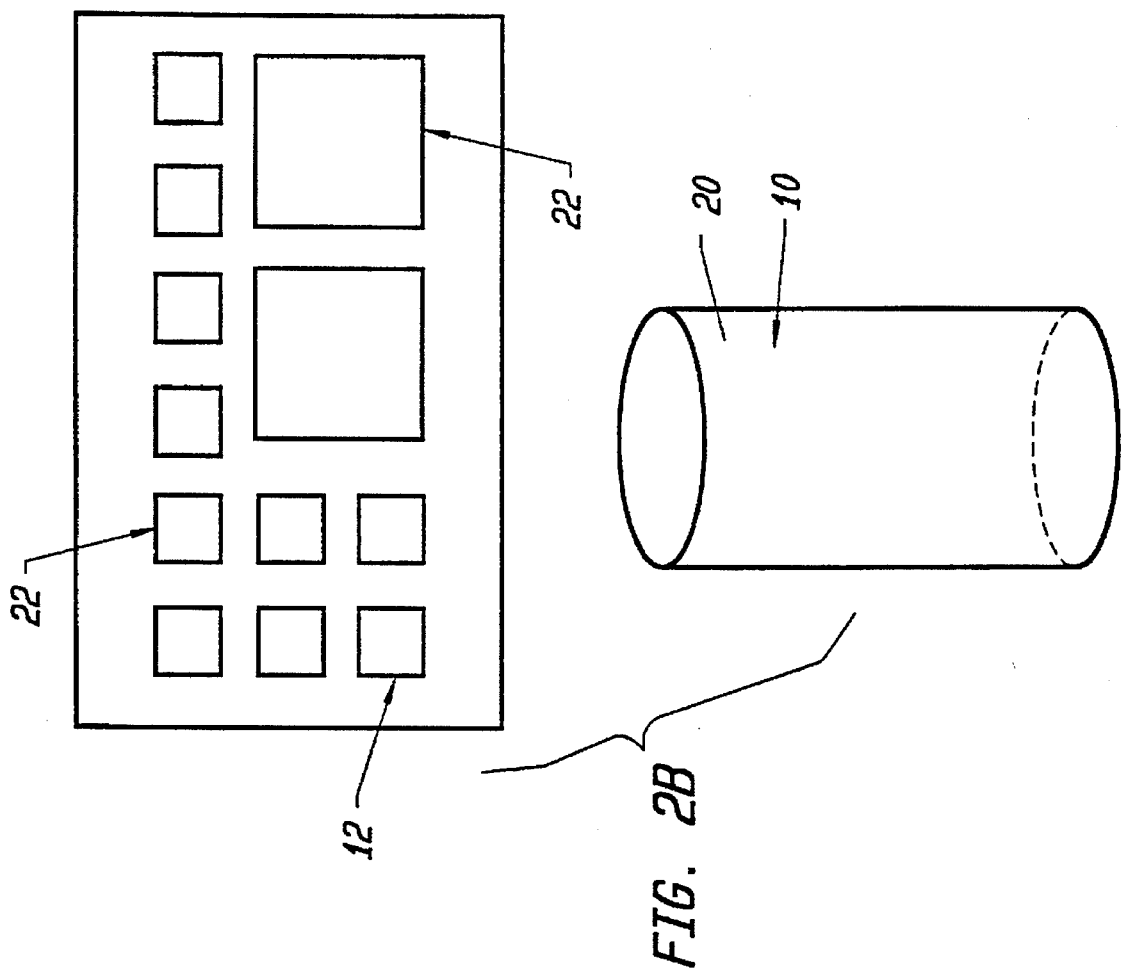
FIGS. 2A–B provide examples of carrousel/screen holder combinations which may be used with the screen reading system of the present invention.
Figure 2A:
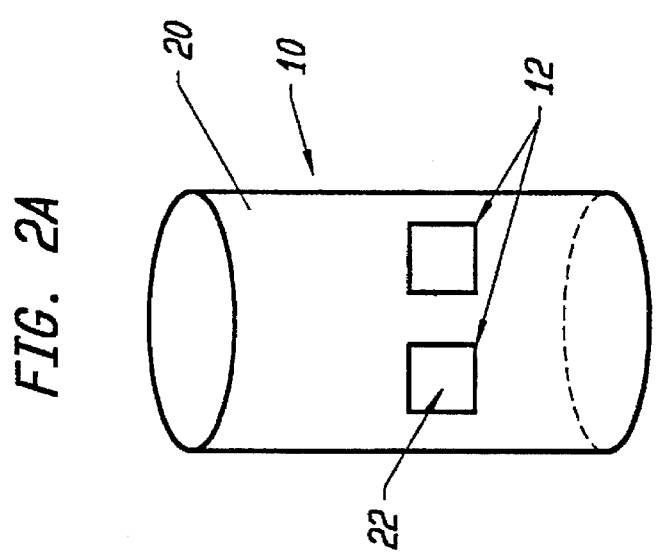

FIGS. 2A–B provide examples of carrousel 10/screen holder 12 combinations which may be used with the screen reading system of the present invention. As illustrated in FIG. 2A, the screen holder 12 and the carousel 10 may form an unified body where the carousel 10 is removable from the screen scanning system 16. FIG. 2A illustrates the carrousel 10 as a cylindrically shaped drum 20 which includes a series of screen holding mechanisms 22 built into the wall of the drum 20, the screen holding mechanisms 22 combining to form the screen holder 12. Alternatively, as illustrated in FIG. 2B, the screen holder may be a series of screen holding mechanisms 22 which can be removably attached to the carrousel 10, for example by wrapping the series of screen holding mechanisms 22 around the carrousel 10. As illustrated in FIG. 2B, screen holding mechanisms 22 of more than one size may be used.

A variety of screen holding mechanisms 22 may be used to attach screen to the screen holder 12. For example, the screen holding mechanism 22 may include an adhesive. Alternatively, an adhesive may be mounted onto the screen. As illustrated in FIG. 3A, complementary physical anchoring elements 24, 25 may be incorporated onto the screen holder 12 and the back of the screen 14 such that the screen 14 is held in place by the union of the complementary anchoring elements 24, 25. As illustrated in FIG. 3B the screen holding mechanism 22 may include a ferromagnetic material, most commonly an iron based compound, which causes a screen 14 containing a magnet 27 to adhere to the screen holding mechanism 22 incorporated into the screen holder 14. Alternatively, the screen holding mechanism 22 may include magnetic material which adheres to ferromagnetic material incorporated into a screen. Use of either magnetic, adhesive or anchor mounting provides the advantage that none of the screen's surface is obstructed, thereby providing the maximum readable area.

Figure 3C:
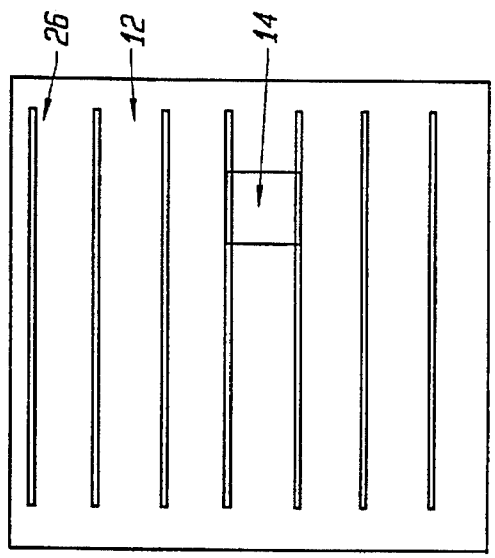
FIGS. 3A–C illustrate mechanisms for mounting a screen on a screen holder.
Figure 3B:
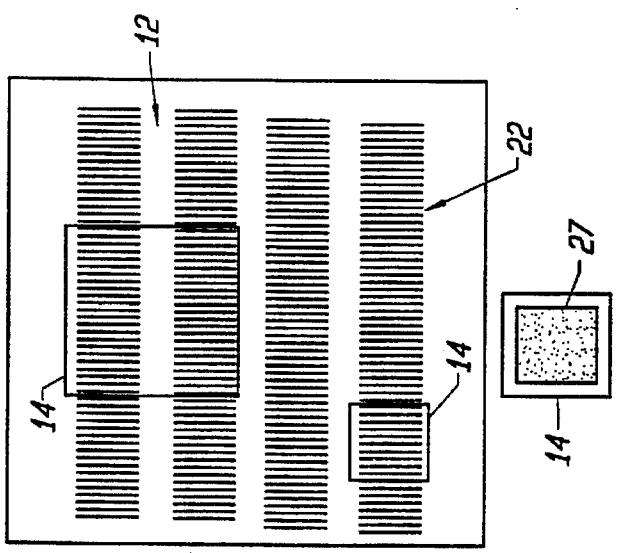
Figure 3A:
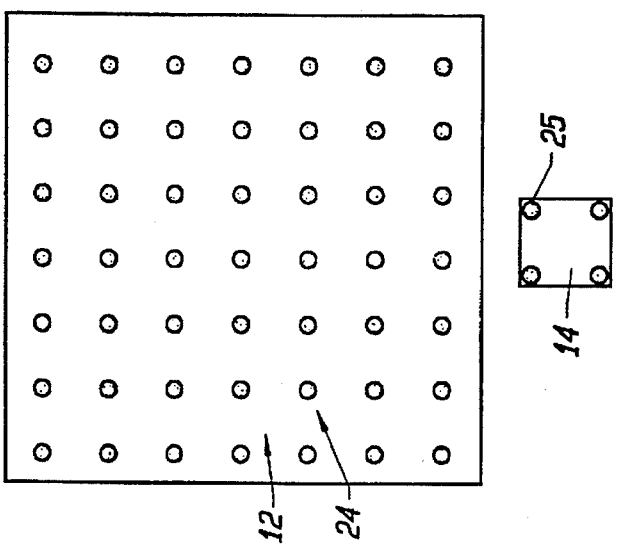

As illustrated in FIG. 3C, the screen holder 12 may alternatively include guide rails 26 between which the screen 14 is positioned in order to mount the screen onto the screen holder 12. A variety of other mechanisms for attaching the screen 14 to the screen holder 12 may be envisioned by one of ordinary skill in the art and are intended to fall within the scope of the present invention.

Screens that may be used in conjunction with the screen reading system of the present invention include any screen having a storage layer. The storage layer may be formed of any compound which absorbs radiation, such as x-rays, α-rays, β-rays, γ-rays, cathode rays and ultraviolet rays, and which, when stimulated by suitable electromagnetic wave radiation, emits electromagnetic wave radiation of a different frequency.

The storage layer is preferably a storage luminophore and is most preferably a stimulable phosphor. The stimulable phosphor is preferably stimulated by light having a wavelength between about 590 and 700 nm. The stimulable phosphor also preferably emits light energy at a wavelength greater than 300 nm, more preferably greater than 390 nm. The stimulable phosphor is also preferably stimulated by light having a wavelength at least 50 nm larger than light emitted from the storage layer.

With regard to the use of a storage layer radiation screen in dental radiography, it is preferred that the screen include a heavy metal layer which serves to reduce the amount of X-ray radiation traversing the radiographic screen into the patient. The heavy metal layer is also preferably provided with a pattern, the appearance of which on the image read indicates that the screen was placed in the patient's mouth with the heavy metal layer facing toward the radiation imaging source. The screen also preferably includes a waterproof coating which is resistant to mild cleaning solutions of the types which are commonly used to disinfect screens of this nature, thereby enabling their reuse. A patient identification system, such as a bar code, may also be incorporated onto the screen or stored onto the storage layer during exposure.

Figure 4:
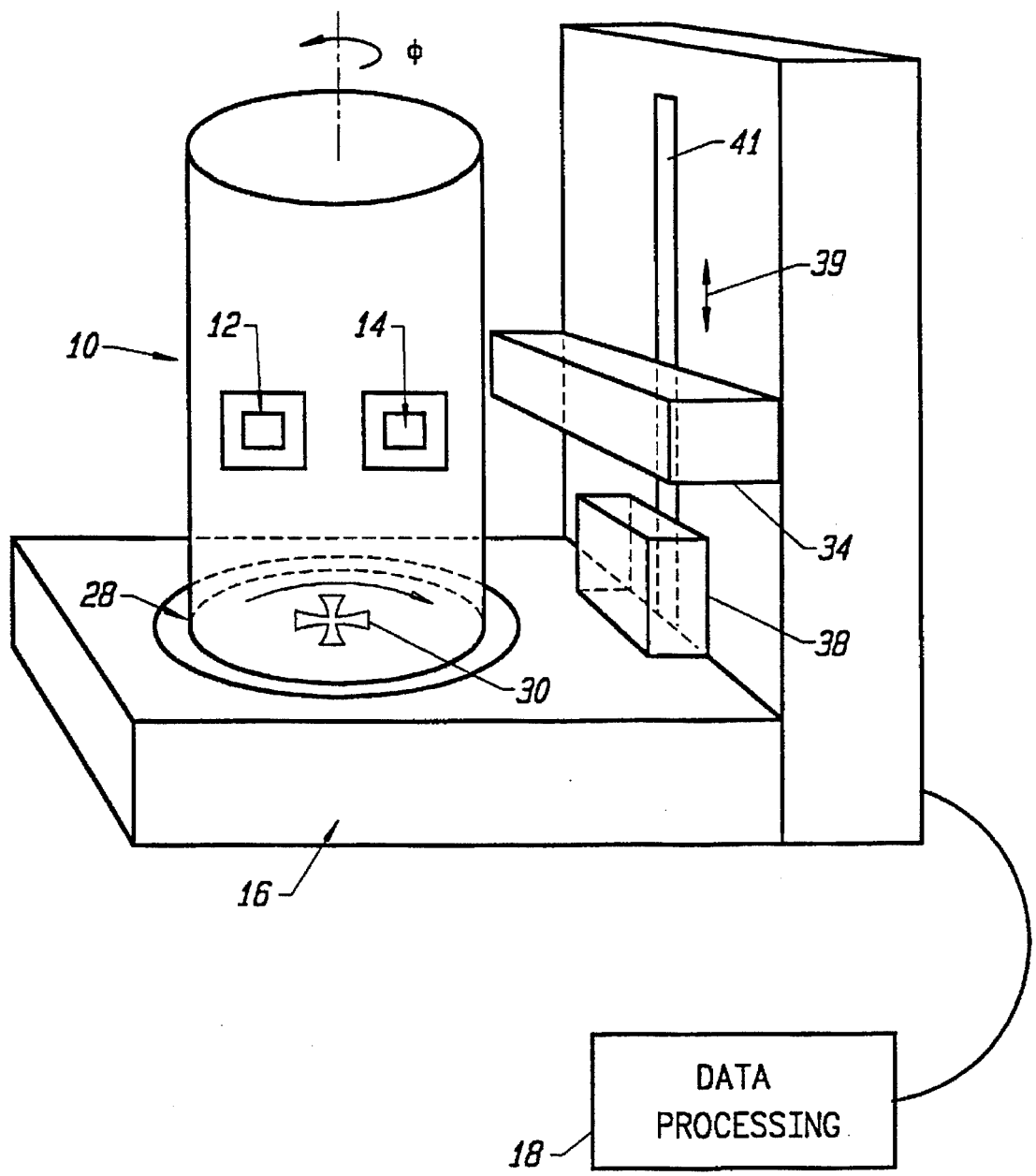
FIG. 4 illustrates a screen scanning system for use in the screen reading system of the present invention.

A more detailed depiction of the screen scanning system 16 is provided in FIG. 4. As illustrated in FIG. 4, the screen scanning system 16 includes a carousel mount 28 on which a removable or fixed carousel 10 is mounted and rotated. Attached to the carousel mount 28 is a mechanism 30 for rotating the carousel 10.

Also included in the screen scanning system 16 is an image acquisition optical system 34 which reads the image stored on the screen 14 as the screen is rotated on the carousel 10 past the image acquisition optical system 34. The image acquisition optical system 34 is preferably positioned within about 3–10 mm of the circumference of the circle 36 formed by the path of the screen 14 on the rotating carousel 10. The image acquisition optical system 34 is attached to an optics driver 38 such that the image acquisition optical system 34 may be moved in a direction 39 which is parallel to the carousel's rotational axis $\phi$. Alternatively, the carousel may be moved in a direction 39 parallel to the carousel's rotational axis $\phi$ in order to cause the effective motion of the image acquisition optical system 34 in a direction parallel to the carousel's rotational axis $\phi$. It should be further noted that rotation of the carousel 10 and movement of the image acquisition optical system 34 relative to the carousel 10 in a direction parallel to the carousel's rotational axis $\phi$ may be performed by different motors or by a single motor.

Figure 5:
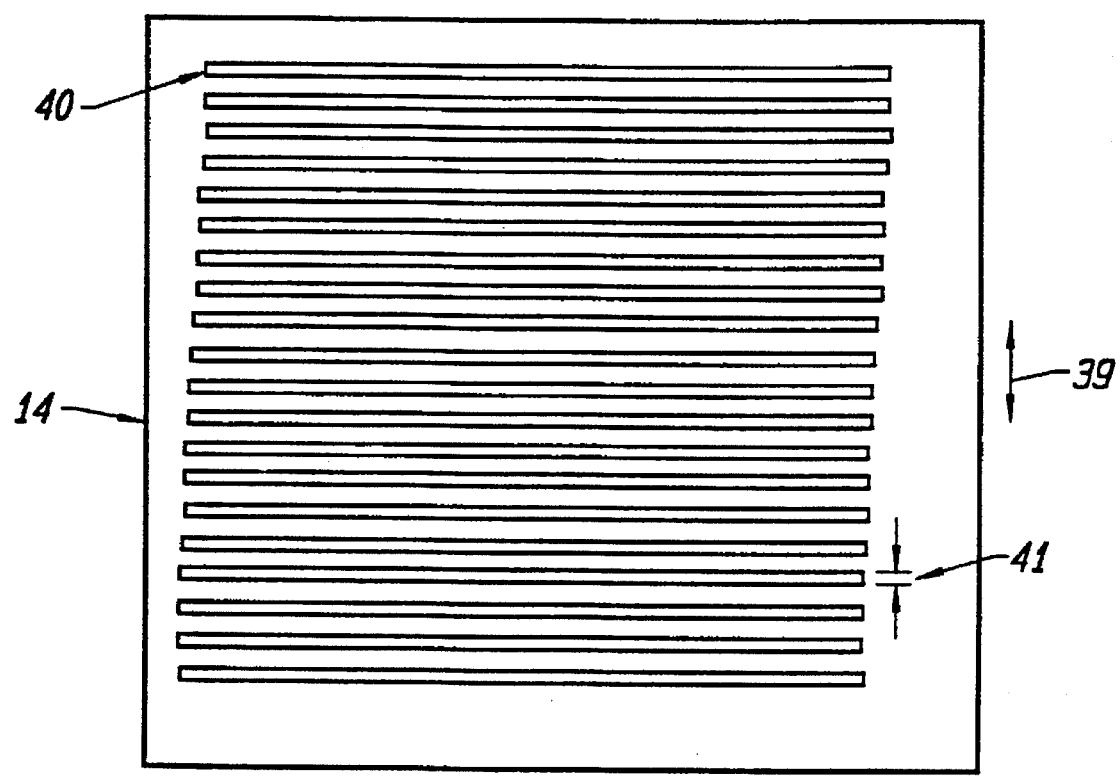
FIG. 5 illustrates how the rotation of the carousel causes the screen scanning system to scan over a narrow line-shaped area of the screen perpendicular to the carousel's rotational axis.

As illustrated in FIG. 5, rotation of the carousel 10 causes the screen scanning system to scan over a narrow line-shaped area 40 of the screen 14 perpendicular to the carousel's rotational axis $\phi$. During operation of the screen reading system, the carousel 10 is preferably rotated at a speed of at least 60 revolutions per minute, more preferably at least 300 revolutions per minute. In general, the rate at which the carousel is rotated is dependent on the size of the pixels forming the image being read, the size of the pixels depending on the quality of the storage layer used in the screen and the resolution being sought to be achieved. The maximum speed at which the carousel may be rotated is limited by the balancing of the carousel. In general it is preferable to rotate the carousel at higher rates in order to enable the screens to be scanned at faster rates.

As the screen 14 passes the image acquisition optical system 34 during each revolution of the carousel 10, a different line-shaped portion of the screen 40 is read, the width of the line 41 corresponding to the width of a pixel. The acquisition optical system 34 preferably reads pixels having a width between about 30 and 200 microns, more preferably between about 35 and 50 microns. As the carousel 10 is rotated, the image acquisition optical system 34 is simultaneously moved in a direction 39 parallel to the axis of rotation $\phi$ of the carousel 10 such that a new line-shaped portion 40 of screen 14 is read during each carousel revolution. By moving the image acquisition optical system 34 at an appropriate speed, the image acquisition optical system 34 can be scanned over different narrow line-shaped areas of the screen, thereby enabling the entire surface area of the screen to be scanned. For example, in order to generate an image having a pixel size of 40 microns, the carousel 10 may be rotated at 342 revolutions per minute while the image acquisition optical system 34 is simultaneously moved in a direction 39 parallel to the axis of rotation of the carousel 10 at a rate of about 241 microns per second.

Referring back to FIG. 4, the optics driver 38 used to move the image acquisition optical system 34 in a direction 39 parallel to the axis of rotation $\phi$ of the carousel 10 may include a four phase stepper motor with an encoder that has a lead screw directly mounted onto its shaft. The image acquisition optical system may be mounted onto a linear slide 41 attached to the lead screw nut such that rotation of the lead screw nut causes the image acquisition optical system 34 to move in a direction 39 parallel to the axis of rotation $\phi$ of the carousel 10.

The rotation mechanism 30 for the rotating the carousel 10 may be a direct drive mechanism where the carousel 10 is attached to a motor shaft through an interface plate. The plate may have positioning members such as a loading pin which locates the carousel relative to the start of the scan position, a centration device which centers the carousel on the mount, and/or a locking mechanism which locks the carousel onto the rotation mechanism. The interface plate may also include a variety of other positioning members whose use in combination with the rotation mechanism are within the level of skill in the art.

The rotation mechanism 30 for the carousel 12 may also be an indirect drive mechanism with an interface between the motor and the carousel. One embodiment of an indirect drive mechanism includes a DC motor with belt drive/gears and an encoder configuration which provides the screen reading system with feedback as to the angular position of the carousel. In-direct drive mechanisms provide the advantage of improving the rigidity of the carousel drive mechanism.

Figure 6:
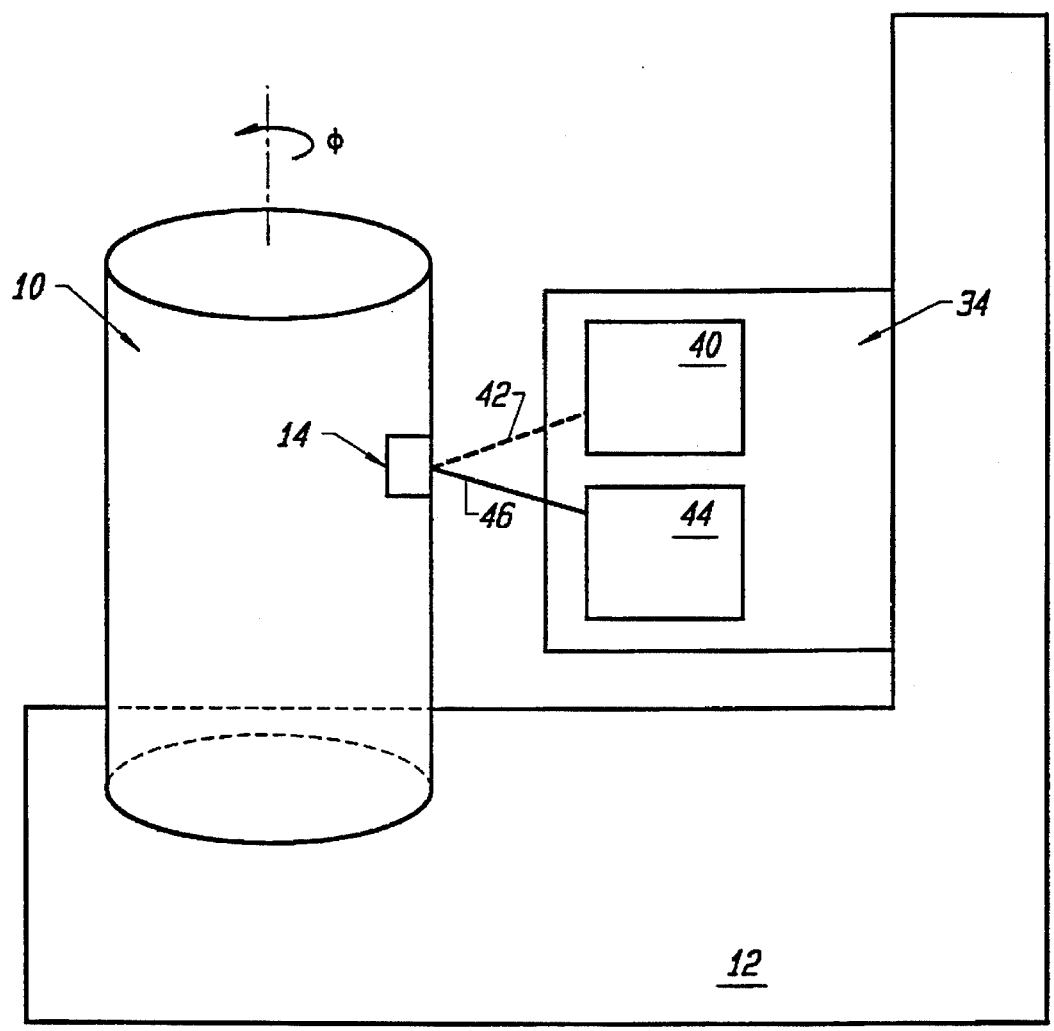
FIG. 6 illustrates the image acquisition optical system.

The image acquisition optical system 34 used to read the image stored on the screen 14 is illustrated in FIG. 6. As illustrated in FIG. 6, the image acquisition optical system 34 includes an illumination system 40 which provides an excitation beam 42 to excite an area of the screen and an emission collecting system 44 which collects light emitted 46 by the screen in response to the excitation of the screen by the excitation beam 42.

The excitation beam produced by the illumination system is generally a narrow diameter beam, preferably between abut 0.002 and 3 mm, with a gaussian distribution (1/e$^2$) between about 1 and 10 mW. The excitation beam also preferably has a wavelength between about 590 and 700 nm, more preferably between about 590 and 640 nm.

In order to produce the necessary excitation beam 42, the illumination system 40 generally includes an illumination source, such as a laser diode, as well as series of optics which correct the output of the illumination source.

Figure 7:
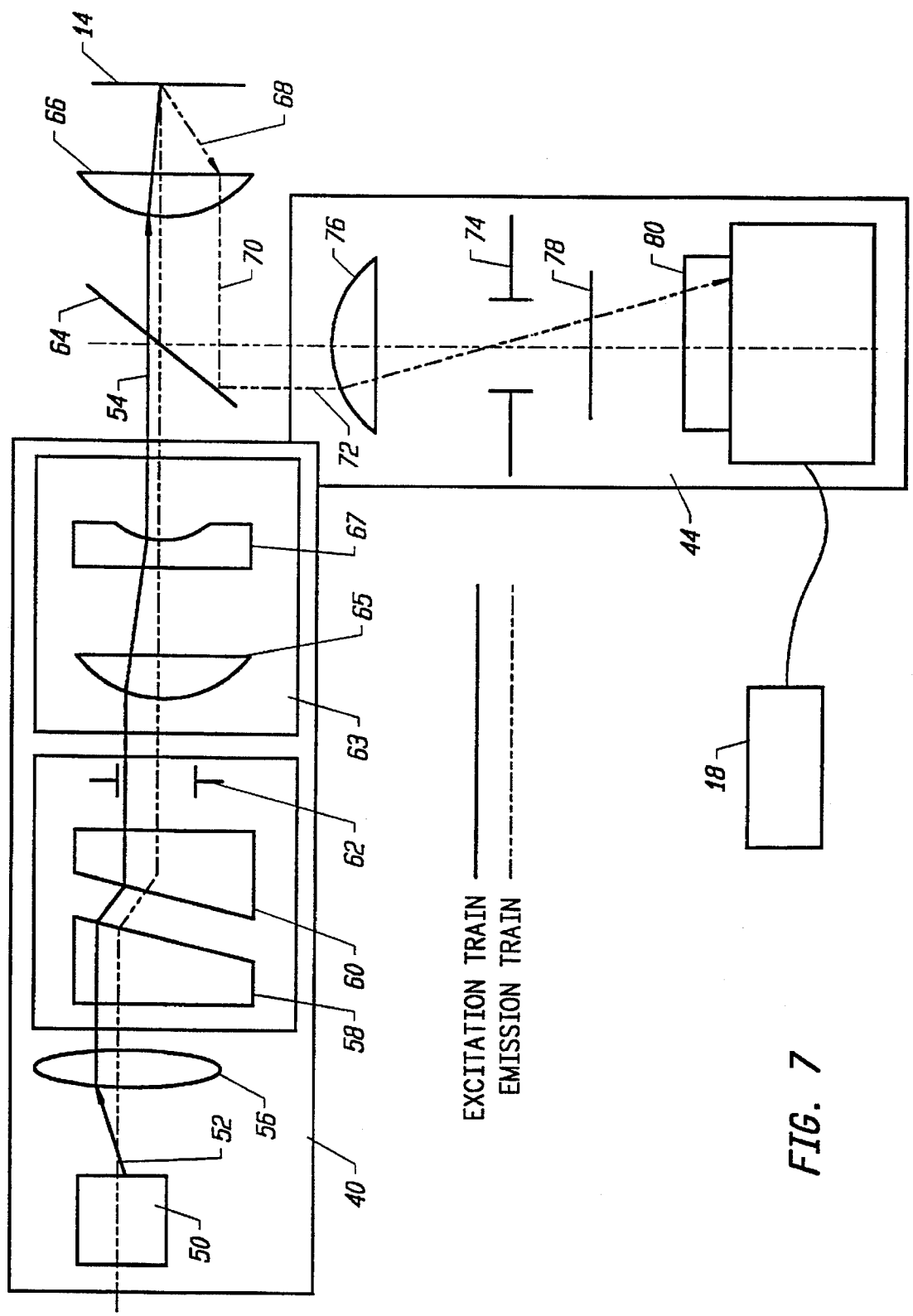
FIG. 7 illustrates an example of an illumination system and an emission collection system that may be used in the image acquisition optical system.

An example of an illumination system 40 and an emission collecting system 44 which may be used in the image acquisition optical system 34 are illustrated in FIG. 7. The illumination system 40 includes a laser diode 50, such as a HeNe laser, whose output is preferably controlled at a constant light output mode utilizing internal diode for automatic servo control. The output power of the laser diode is preferably between about 1 and 10 mW@635 nm, the emission of the storage layer being proportional to the strength of the excitation beam 42 on the screen. The intensity of the excitation beam 42 on the screen is preferably 2.4×10$^4$ ergs/cm$^2$.

The laser diode 50 produces an elliptical and astigmatic beam 52 which is corrected by a series of lenses to produce a round excitation beam 54. As illustrated in FIG. 7, these lenses include a collimating aspheric lens 56, a pair of anamorphic prisms 58, 60 and/or a telescope 63 with an aperture 62. A pair of cylindrical lenses can be used in place of the collimating aspheric lens 56 and pair of anamorphic prisms 58, 60. The focal plane 64 of the collimating aspheric lens 56 is set at the excitation plane of the laser diode 50 to form an elliptical excitation beam 52 with a minimum diameter of 2 mm. The specific optical characteristics of the collimating aspheric lens varies depending on the laser diode employed. The pair of anamorphic prisms 58, 60 reshapes the elliptical beam 52 into a round excitation beam 54.

The diameter of the excitation beam 54 is further reduced using a telescope 63 which preferably reduces the diameter of the excitation beam 54 to between about 1 and 0.2 mm. In one embodiment, the telescope 63 consists of a plano convex lens 65 with a focal length of 30 mm and a plano concave lens 67 with a focal length of 6 mm.

The excitation beam 54 produced by the telescope 62 is then passed through a dichroic beam splitter 64 which transmits a high percentage of excitation beam 54, preferably at least 90%, more preferably at least 95%. The dichroic beam splitter 64 is preferably constructed of BK-7 glass with a dichroic coating.

An objective lens 66 is also employed which focuses the excitation beam 54 onto the screen 14. The objective lens 66 may be a spherical or an aspherical lens. The objective lens 66 is preferably an aspherical lens which focuses the excitation beam 54 onto a spot on the screen having a diameter of between about 30 and 200 microns, more preferably 35 and 50 microns, the diameter of the spot corresponding to the diameter of the pixel being read. The minimum size of the spot on which the excitation beam 54 is focused is dependent on the amount of carousel run out during rotation, a smaller amount of carousel run out enabling the excitation beam 54 to be focused on a smaller spot on the screen.

The excitation beam 54 focused on the screen 14 induces an emission of light 68 at a different wavelength than the excitation beam 54. The wavelength of the emitted light is lower when a layer of a stimulable phosphor is employed and higher when a layer of fluorescent material is employed. The intensity of the light 68 emitted by the screen is proportional to the amount of radiation absorbed by the screen during exposure.

The light emitted 68 from the screen 14 is collected by the emission collecting system 44, also illustrated in FIG. 7. In addition to focusing the excitation beam 54 on a spot on the screen 14, the objective lens 66 also serves to collect and collimate the light 68 emitted from the screen 14. The focused emission light 70 is then reflected off the dichroic beam splitter 64 which reflects a high percentage of the light emitted 68 by the screen 14, preferably at least 90%, more preferably at least 95%.

The reflected emitted light 72 is refocused onto an aperture 74 by imaging lens 76. The aperture 74 serves to enhance the signal to noise ratio of the image acquisition optical system 34 by excluding light not corresponding to the light emitted from the sample, such as reflected excitation light. The diameter of the aperture 74 is preferably adjustable so that the signal to noise ratio generated by the image acquisition optical system can be optimized.

A portion of the light traversing the aperture 74 corresponds to reflected excitation light which can be eliminated by the inclusion of a color filter 78 which transmits the emission light while blocking most of the reflected excitation light.

Light that is transmitted through the aperture 74 is then received by a photodetector 80 which converts the photons of energy received into an electrical signal. The electrical signal produced by the photodetector 80 is then conveyed to a data processing system 18 for processing of the electronic signal generated by the photodetector 80.

The photodetector 80 is preferably a photo multiplier tube (PMT) which is useful for optimizing low light level collection. Examples of other photodetectors which may be used in the image acquisition optical system 34 include a cooled metal silicon, avalanche photo diode or pin diode. Alternate types of detectors may also be used in the image acquisition optical system 34 and are intended to fall within the scope of the present invention.

In an alternate embodiment of the screen scanning system 16, an automated carousel mount 80 is employed on which two or more carrousels 10 may be mounted and automatically moved into position to be read by the image acquisition optical system 34. According to this embodiment, multiple carrousels, each holding a series of screens, can be loaded at one time on the screen scanning system 16. This greatly increases the number of screens which can be read by the screen scanning system 16 without intervention by the user.

Figure 8:
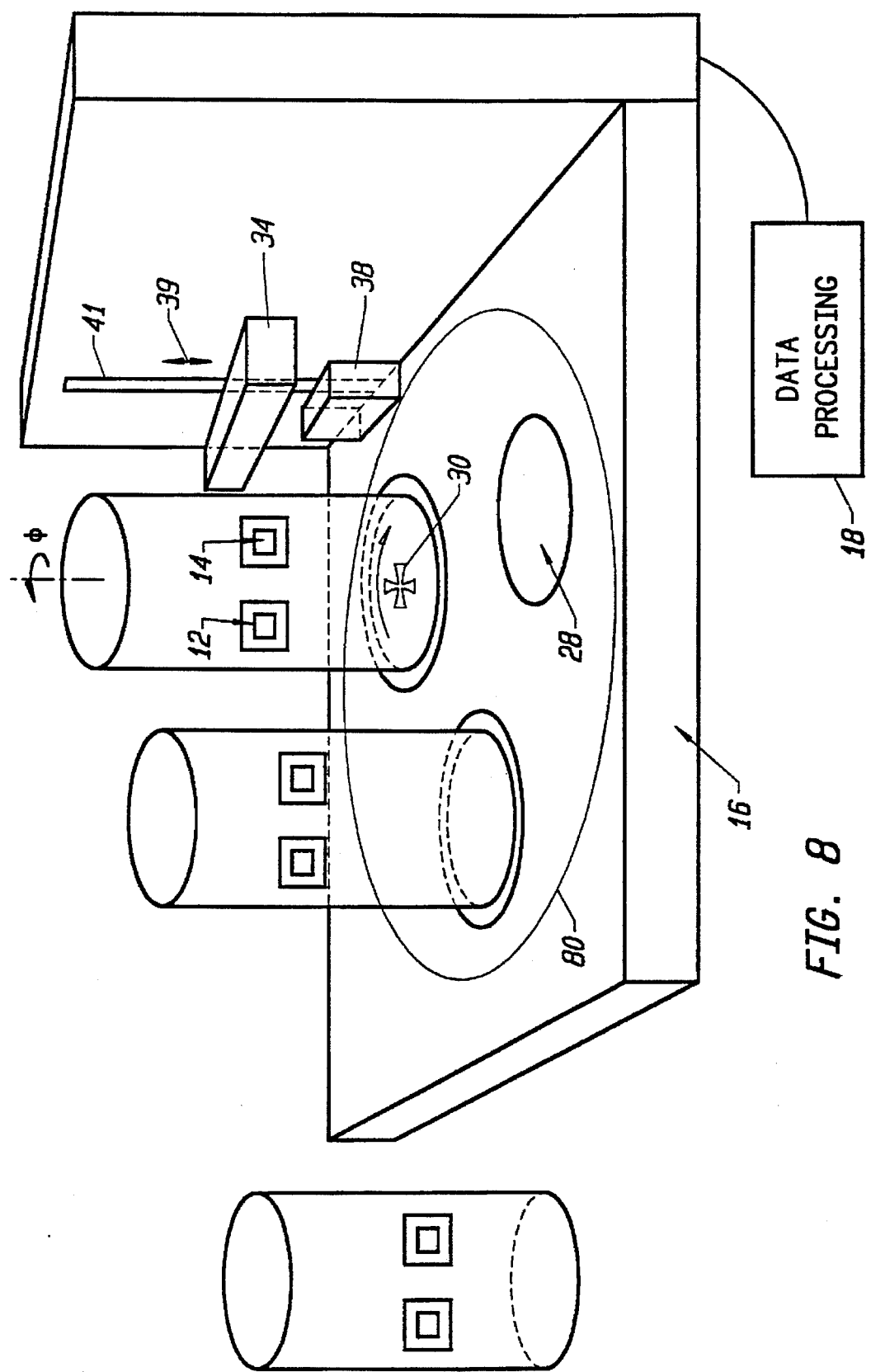
FIG. 8 illustrates an embodiment of the screen scanning system which uses an automated carousel mount.

An embodiment of a screen scanning system 16 including an automated carousel mount 80 is illustrated in FIG. 8. As illustrated in FIG. 8, the automated carousel mount 80 itself forms a carousel-like series of carousel mounts 28 on which a series of carrousels 10 may be placed. The automated carousel mount 80 may be rotated such that a specific carousel 10 is moved into position to be read by the image acquisition optical system 34. According to this embodiment, once a particular carousel has been read, the automated carousel mount 80 rotates to move a different carousel 10 into position to be read by the image acquisition optical system 34.

In response to the excitation beam 42, the screen emits an emission beam 46 which is focused by the emission collecting system 44 onto a photodetector 80. The photodetector 80 generates an electrical signal in response to the emission beam 46 collected which is then conveyed to the data processing system 18.

Figure 9:
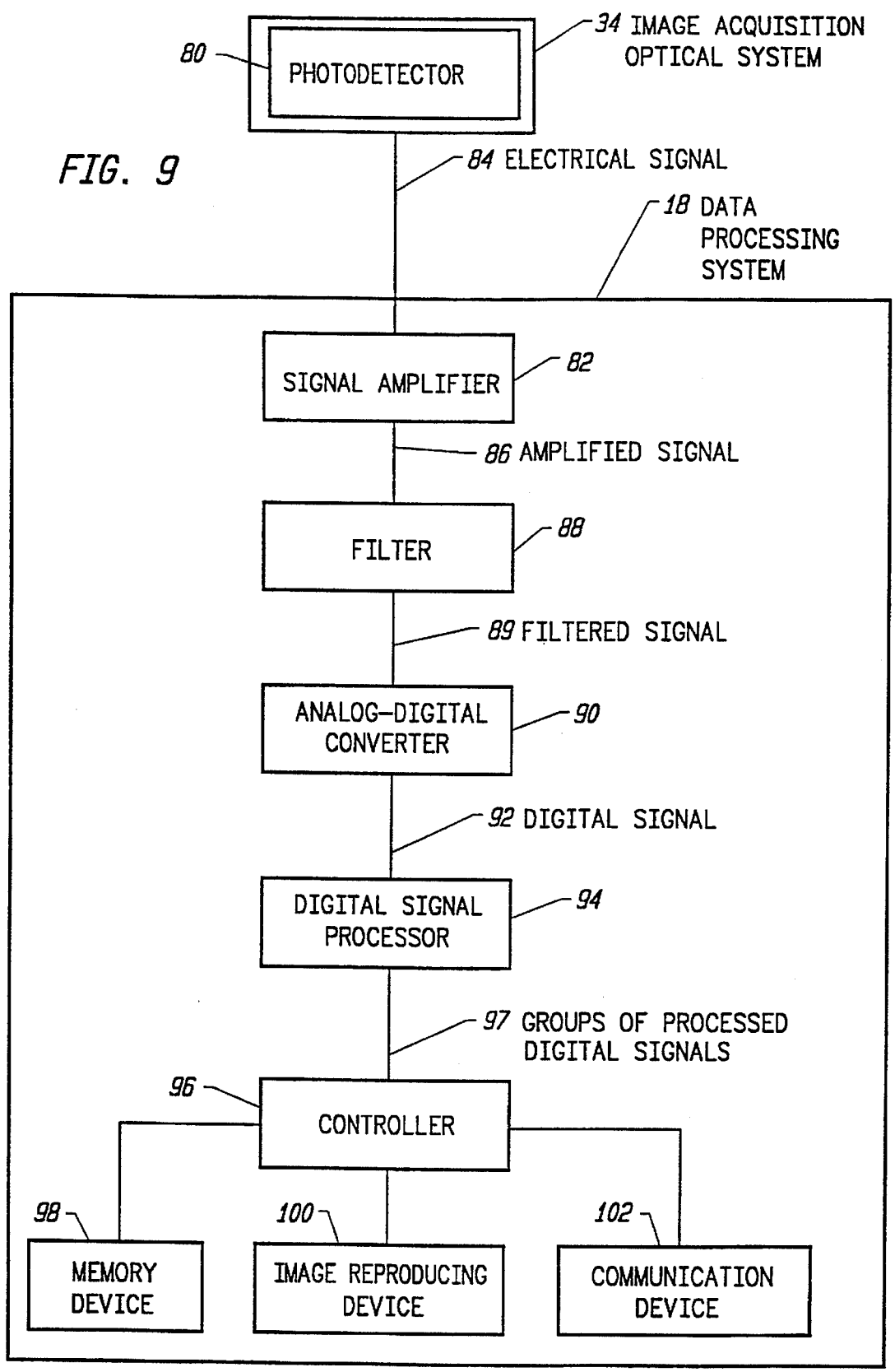
FIG. 9 illustrates a block diagram of an embodiment of a data processing system which may be used with the screen reading system of the present invention.

An embodiment of a data processing system 18 which may be used with the screen reading system of the present invention is illustrated in FIG. 9. It should be noted, however, that a variety of systems may be designed to convert the electrical signal generated by the photodetector 80 into computer readable data corresponding to the image read from the screen.

As illustrated in FIG. 9, the data processing system 18 includes a signal amplifier 82 which amplifies the electrical signal 84 generated by the photodetector 80. The intensity of the electrical signal generated by the photodetector 80 is a function of the emission beam 46 generated by the screen which, in turn, is dependent on such factors as the particular storage layer used, the intensity of the excitation beam 42 and the exposure intensity of the screen. The signal amplifier 82 may optionally be omitted from the data processing system 18.

The amplified signal 86 is passed through a filter 88, such as a low pass filter, which serves to reduce the amount of noise in the amplified signal. The filtered signal 89 is then transmitted to an analog-to-digital converter 90 which converts the filtered signal 89 into a digital signal 92. The sampling rate of the analog-to-digital converter 90 is set at a rate such that one or more data samples are collected per pixel of screen read.

The digital signals 92 from the analog-to-digital converter 90 are conveyed to a digital signal processor 94 which processes the one or more data samples and conveys the digital signals 92 to a controller 96. The digital signal processor 94 preferably has a buffering capacity such that groups of processed digital signals 97 corresponding to the pixels 98 on the screen are periodically spooled to the controller 96.

The groups of digital signals corresponding to the pixels 97 are then buffered in the controller 96 and written to memory (hard disk, floppy, etc.) 98, for example in form of a "TIFF" file. The data can also be conveyed to an image reproducing device 100 (monitor, printer), as well as a variety of communication devices 102 (modem, network).

The screen reading system may also include a screen erasing mechanism for releasing any radiation energy remaining on the screens after the screens are read. In general, the screen erasing mechanism includes a high intensity light source which provides erasing light at a wavelength suitable for exciting the storage layer to cause the emission of any radiation energy stored on the screen. The erasing light preferably has the same wavelength as the excitation beam.

In one embodiment, the screen erasing mechanism is positioned such that the erasing light erases portions of the screen as those portions are read. Alternatively, the screen erasing mechanism may focus erasing light on the screen after the entire screen has been read.

The foregoing examples and description of preferred embodiments of the present invention are provided for the purposes of illustration and description. The examples and preferred embodiments, however, are not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A system for reading multiple storage layer radiation screens, the system comprising:
    a carousel for holding multiple storage layer radiation screens;
    a rotation mechanism for rotating the carousel about a rotational axis, rotation of the carousel causing each screen on the carousel to move in a circular path about the rotational axis;
    an image acquisition optical system positioned adjacent the carousel, the image acquisition optical system including an excitation system for focusing an excitation beam in the direction of the carousel, the excitation beam causing light to be emitted from those screens which are contacted with the excitation beam as the carousel is rotated, and an emission collecting system for collecting the light emitted from the screens; and
    an optics driver for moving the excitation beam in a direction parallel to the rotational axis of the carousel as the carousel is rotated.

2. The system according to claim 1 wherein the image acquisition optical system is positioned within about 20 mm of the circular path of the screen.

3. The system according to claim 2 wherein the image acquisition optical system is positioned within about 10 mm of the circular path of the screen.

4. The system according to claim 1 wherein the excitation beam has a diameter between about 30 and 200 microns where the excitation beam contacts the screen.

5. The system according to claim 4 wherein the excitation beam has a diameter between about 35 and 50 microns where the excitation beam contacts the screen.

6. The system according to claim 1 wherein the rotation mechanism rotates the carousel at least about 60 revolutions per minute.

7. The system according to claim 6 wherein the rotation mechanism rotates the carousel at least about 300 revolutions per minute.

8. The system according to claim 1 wherein the multiple storage layer radiation screens include screens of at least two different sizes.

9. The system according to claim 1 wherein the carousel includes at least one screen holder for holding at least one of the multiple storage layer radiation screens, the screen holder being removable from carousel.

10. The system according to claim 9 wherein the the carousel includes at least two screen holders.

11. The system according to claim 9 wherein the at least two screen holders hold storage layer radiation screens of at least two different sizes.

12. The system according to claim 1 wherein the carousel is removable from the system.

13. The system according to claim 1 wherein the system further includes an erasing mechanism for erasing portions of the screen after being read by the image acquisition optical system.

14. The system according to claim 1 wherein the carousel includes an element for binding the screen to the carousel, the binding element being selected from the group consisting of a magnet, a ferromagnetic material, a clip, an adhesive and a plurality of physical anchoring elements.

15. A system for reading multiple storage layer radiation screens, the system comprising:
    a carousel mount on which multiple carousels are mountable, each carousel being movable on the mount to a position where the carousel is rotated by a rotation mechanism;
    a rotation mechanism for rotating at least one carousel on the carousel mount about a rotational axis to cause a screen held on the rotating carousel to move in a circular path about the rotational axis; and
    an image acquisition optical system positioned adjacent the rotating carousel, the image acquisition optical system including an excitation system for focusing an excitation beam in the direction of the rotating carousel, the excitation beam causing light to be emitted from the screen as the screen is contacted with the excitation beam as the carousel is rotated, and an emission collecting system for collecting the light emitted from the screen.

16. The system according to claim 15 wherein the carousel mount includes a mechanism for moving each of the multiple carousels on the carousel mount to the position where the carousel is rotated by the rotation mechanism.

17. The system according to claim 15 wherein the screen scanning system further includes an optics driver which moves the excitation beam in a direction parallel to the rotational axis of the carousel as the carousel is rotated.

18. The system according to claim 15 wherein the image acquisition optical system is positioned within about 20 mm of the circular path of the screen.

19. The system according to claim 15 wherein the excitation beam has a diameter between about 30 and 200 microns where the excitation beam contacts the screen.

20. The system according to claim 19 wherein the excitation beam has a diameter between about 35 and 50 microns where the excitation beam contacts the screen.

21. The system according to claim 15 wherein the rotation mechanism rotates the carousel at least about 60 revolutions per minute.

22. The system according to claim 15 wherein the system further includes an erasing mechanism for erasing portions of the screen after being read by the image acquisition optical system.

23. The system according to claim 15 wherein the system includes at least one carousel for holding a storage layer radiation screen.

24. The system according to claim 23 wherein the at least one carousel holds multiple storage layer radiation screens.

25. The system according to claim 24 wherein the multiple storage layer radiation screens include screens of at least two different sizes.

26. The system according to claim 23 wherein the at least one carousel is removable from the carousel mount.

27. The system according to claim 26 wherein the at least one carousel holds multiple storage layer radiation screens.

28. The system according to claim 27 wherein the multiple storage layer radiation screens include screens of at least two different sizes.

29. A method for reading multiple storage layer radiation screens comprising:

rotating a carousel holding multiple storage layer screens about a rotational axis such that the multiple screens move in circular paths about the rotational axis;

focusing an excitation beam in the direction of the carousel as the carousel is rotated, the excitation beam causing light to be emitted from those screens which move into contact with the excitation beam as the carousel is rotated;

collecting the light emitted; and moving the excitation beam in a direction parallel to the rotational axis of the carousel as the carousel is rotated.

30. The method according to claim 29 wherein the excitation beam has a diameter between about 30 and 200 microns where the excitation beam contacts the screen.

31. The method according to claim 29 wherein the carousel is rotated at least about 60 revolutions per minute.

32. The method according to claim 29 wherein the multiple storage layer radiation screens are of at least two different sizes.

33. The method according to claim 29, wherein the carousel includes one or more elements for binding the multiple screens to the carousel, the one or more binding elements being selected from the group consisting of a magnet, a ferromagnetic material, a clip, an adhesive and a plurality of physical anchoring elements, the method further including the step of attaching the screen to the carousel by contacting the one or more binding elements on the carousel to a complementary binding element on the screen.

34. A system for reading a storage layer radiation screen, the system comprising:

a carousel mount for holding a carousel having a storage layer radiation screen such that the carousel is removable from the mount without disassembly of the mount, the carousel mount including a rotation mechanism for rotating the carousel about a rotational axis, rotation of the carousel causing the screen on the carousel to move in a circular path about the rotational axis;

an image acquisition optical system positioned adjacent the carousel, the image acquisition optical system including an excitation system for focusing an excitation beam in the direction of the carousel, the excitation beam causing light to be emitted from the screen as the screen is contacted with the excitation beam as the carousel is rotated, and an emission collecting system for collecting light emitted from the screen; and an optics driver for moving the excitation beam in a direction parallel to the rotational axis of the carousel as the carousel is rotated.

35. A method for forming and reading an image on a storage layer radiation screen comprising:

forming an image on a storage layer screen;

attaching the storage layer screen to a carousel;

attaching the carousel containing the storage layer screen to a mechanism for rotating the carousel about a rotational axis;

rotating the carousel about the rotational axis, rotation of the carousel causing the screen on the carousel to move in a circular path about the rotational axis;

focusing an excitation beam in the direction of the carousel as the carousel is rotated, the excitation beam causing light to be emitted from the screen when the screen is contacted with the excitation beam as the carousel is rotated;

collecting the light emitted; and moving the excitation beam in a direction parallel to the rotational axis of the carousel as the carousel is rotated.

* * * * *